United States Patent
Heni et al.

(10) Patent No.: US 11,737,649 B2
(45) Date of Patent: Aug. 29, 2023

(54) APPARATUS FOR HEAT DISSIPATION AND USE OF SUCH APPARATUS

(71) Applicant: KARL STORZ SE & Co. KG, Tuttlingen (DE)

(72) Inventors: Andreas Heni, Tuttlingen (DE); Markus Kupferschmid, Tuttlingen (DE); Daniel Ulmschneider, Tuttlingen (DE); Jonas Forster, Tuttlingen (DE)

(73) Assignee: KARL STORZ SE & Co. KG, Tuttlingen (DE)

(*) Notice: Subject to any disclaimer, the term of this patent is extended or adjusted under 35 U.S.C. 154(b) by 269 days.

(21) Appl. No.: 17/010,958

(22) Filed: Sep. 3, 2020

(65) Prior Publication Data
US 2021/0068644 A1 Mar. 11, 2021

(30) Foreign Application Priority Data
Sep. 5, 2019 (DE) .................... 10 2019 123 908.7

(51) Int. Cl.
*F28F 13/00* (2006.01)
*A61B 1/00* (2006.01)
(Continued)

(52) U.S. Cl.
CPC ........... *A61B 1/0008* (2013.01); *A61B 1/012* (2013.01); *A61B 1/05* (2013.01); *A61B 1/128* (2013.01);
(Continued)

(58) Field of Classification Search
CPC .......... F28F 2013/005; F28F 2013/006; F28F 2013/008; F28F 13/00; A61B 1/128;
(Continued)

(56) References Cited

U.S. PATENT DOCUMENTS 3,391,728 A * 7/1968 Kelly ............... G05D 23/22
165/277
4,770,242 A * 9/1988 Daikoku ............ H01L 23/4338
257/713
(Continued)

FOREIGN PATENT DOCUMENTS

DE 102010024003 A1 12/2011
DE 102014105680 B3 * 5/2015 ............ F24S 10/95
(Continued)

OTHER PUBLICATIONS

WO-2017008748-A1 (Year: 2017).*
(Continued)

*Primary Examiner* — Jenna M Hopkins
(74) *Attorney, Agent, or Firm* — Jason H. Vick; Sheridan Ross, PC

(57) ABSTRACT

An apparatus configured for heat dissipation that includes a heat source, a heat sink and a heat conducting element. The heat conducting element conducts heat energy from the heat source to the heat sink along a heat conducting path, and the heat conducting element is arranged in such a way on the heat source and the heat sink and is configured to physically change in such a way with increasing temperature of the heat conducting element that: a) a first cross-sectional area between the heat source and the heat conducting element and/or a second cross-sectional area between the heat conducting element of the heat sink increases, and/or b) a length of the heat conducting path shortens. Further, a video endoscope having such an apparatus and a use of such an apparatus is provided.

2 Claims, 4 Drawing Sheets

(51) Int. Cl.
*A61B 1/012* (2006.01)
*A61B 1/05* (2006.01)
*A61B 1/12* (2006.01)
*H05K 7/20* (2006.01)

(52) U.S. Cl.
CPC .......... *F28F 13/00* (2013.01); *H05K 7/2039* (2013.01); *F28F 2013/008* (2013.01); *F28F 2280/10* (2013.01)

(58) Field of Classification Search
CPC ..... A61B 1/12; A61B 1/0008; A61B 1/00097; A61B 1/012; A61B 1/05; A61B 1/00119; H04N 2005/2255; F28D 2021/005; G05D 23/08; G05D 23/10; G05D 23/1854; G05D 23/1852; G05D 23/02
See application file for complete search history.

(56) References Cited

U.S. PATENT DOCUMENTS

| | | | |
|---|---|---|---|
| 9,510,744 B2 | 12/2016 | Schrader et al. | |
| 10,823,953 B2 | 11/2020 | Kuhn et al. | |
| 11,089,953 B2 * | 8/2021 | Deyanov | A61B 1/128 |
| 2005/0074666 A1 * | 4/2005 | Kimiya | G05D 23/08 |
| | | | 429/62 |
| 2007/0030656 A1 * | 2/2007 | Ross | H05K 7/2049 |
| | | | 361/710 |
| 2010/0147497 A1 * | 6/2010 | Furman | H01L 23/433 |
| | | | 165/185 |
| 2014/0137570 A1 * | 5/2014 | Hauck | H01L 35/30 |
| | | | 62/3.2 |
| 2015/0335233 A1 * | 11/2015 | Pilz | A61B 1/00128 |
| | | | 600/101 |
| 2017/0258309 A1 * | 9/2017 | Deyanov | A61B 1/00071 |
| 2019/0179351 A1 * | 6/2019 | Andres | H01M 10/613 |

FOREIGN PATENT DOCUMENTS

| | | | | |
|---|---|---|---|---|
| DE | 102014107205 A1 | | 11/2015 | |
| DE | 102014225508 A1 * | | 6/2016 | ............. F28F 13/00 |
| DE | 102017118941 B3 | | 8/2018 | |
| EP | 2946718 A1 * | | 11/2015 | ......... A61B 1/00071 |
| GB | 2581998 A * | | 9/2020 | ............. H01L 23/36 |
| WO | WO-2012175627 A2 * | | 12/2012 | ............. F28D 15/00 |
| WO | WO-2016091427 A1 * | | 6/2016 | ............. F28F 13/00 |

OTHER PUBLICATIONS

Search Report for German Application No. 10 2019 123 908.7, dated May 6, 2020.
European Search Report for corresponding European Patent Application No. 20192007.1, dated Jan. 19, 2021.
U.S. Appl. No. 18/102,934, filed Jan. 30, 2023, Heni et al.
Office Action for corresponding European Patent Application No. 20192007.1, dated Mar. 3, 2023.
Office Action for U.S. Appl. No. 18/102,934, dated May 24, 2023.

* cited by examiner

APPARATUS FOR HEAT DISSIPATION AND USE OF SUCH APPARATUS

CROSS-REFERENCE TO RELATED APPLICATION

This application claims priority from German patent application 10 2019 123 908.7, filed on Sep. 5, 2019. The entire contents of this priority application are incorporated herein by reference.

The present disclosure concerns an apparatus for heat dissipation comprising a heat source, a heat sink and a heat conducting element. The disclosure further relates to the use of such an apparatus for heat dissipation in a videoendoscope.

BACKGROUND

In medical technology, the monitoring and control of temperature and heat, the so-called thermal management, is a great challenge, especially for surgical instruments. Electrical devices and the necessary lighting generate heat loss in a confined space, which can only be dissipated with considerable design effort due to the constricted conditions.

SUMMARY

It is one object of the present disclosure to provide an apparatus for heat dissipation which ensures a reliable alignment of several electronic devices to each other even under constricted spatial conditions. Furthermore, a corresponding use is disclosed.

According to a first aspect, there is provided an apparatus for heat dissipation comprising a heat source, a heat sink and a heat conducting element, wherein the heat conducting element conducts heat energy from the heat source to the heat sink along a heat conducting path, and wherein the heat conducting element is arranged in such a way on the heat source and the heat sink and is configured to physically change in such a way with increasing temperature of the heat conducting element that a) a first cross-sectional area between the heat source and the heat conducting element and/or a second cross-sectional area between the heat conducting element of the heat sink increases, and/or b) a length of the heat conducting path shortens. As used herein, the term "heat source" may correspond to any device associated with a videoendoscope that generates heat, for example, during operation. Examples of heat sources as described herein may include, but is in no way limited to, light sources, chips, sensors, drives, actuators, electronics, other electrical devices, etc., and/or combinations thereof. In some embodiments, the heat source may comprise two or more heat sources (e.g., lights, distal chips, etc.). The heat source may generate heat by passing electrical current through one or more electrical traces, wires, and/or substrates associated therewith. The term "heat sink" as used herein may refer to a heat exchanger. The heat sinks, as described herein, may correspond to thermally conductive materials (e.g., metals, etc.) having a shape or geometry that dissipate heat from the system. In some embodiments, the heat sinks may be kept continuously at a temperature below the temperature of the heat source and, in some cases, well below this temperature. The heat conducting element may correspond to one or more physical structures, members, arms, fingers, teeth, thermal interface materials, etc. disposed between the heat source and the heat sink. The heat conducting elements described herein may facilitate the transfer of heat from the heat source to the heat sink along a controlled path. In some embodiments, the heat conducting elements may comprise thermally conductive materials (e.g., metals, bimetals, etc.) that thermally link the heat source with the heat sink. The heat conducting element transfers heat away from the heat source, for example, in a direction of the heat sink.

The inventors have recognized that there are special challenges in the dissipation of heat from two components which must have an exact position relative to one another (e.g., especially important for optical components or lenses arranged in a housing of a videoendoscope, etc.). For example, in the case of heat dissipation the situation exists that with known apparatuses heat is dissipated from both devices, but it cannot be guaranteed that the devices remain at least approximately at the same temperature. Such a temperature difference can be caused, for example, by the fact that the thermal flow from the first device as heat source to a corresponding heat sink is different from the thermal flow from the second device to the heat sink. Furthermore, it is possible that the two devices, even if they are identical in construction, heat up differently. This presents a new challenge, especially in multi-channel endoscopes or exoscopes, where the optimum alignment and adjustment of two optical channels to each other is also important.

One of the special features is that the heat dissipation is controlled by a passive configuration. The physical principle relied upon here is that the thermal flow between a heat source and a heat sink increases, the greater the cross-sectional area A of the heat conduction path between the heat source with temperature $T_1$ and the heat sink with temperature $T_2$ and/or the shorter the length d of the heat conduction path. This physical background is described with the following formula:

$$\dot{Q} = \alpha \cdot \frac{A}{d} \cdot (T_1 - T_2)$$

In this context, the cross-sectional area is to be understood in particular as the effective cross-sectional area and the length in particular as the effective length. This means that the cross-sectional area and/or the length should be considered as those which influence the thermal flow according to the above formula.

Since the apparatus may be made up only of passive elements, it may be used especially in constricted spaces. In addition, the absence of active elements enables particularly long trouble-free operation. Of course, it is also possible to equip the apparatus shown with additional active components for monitoring and control, such as a temperature sensor or a temperature control of the heat sink. However, for certain applications it may be beneficial that the passive embodiment alone may effect temperature control.

In principle, the temperature control works as follows. If the temperature at the heat source rises, the heat conducting element also heats up. The physical properties of the heat conducting element, including its spatial configuration, are such that the physical change in the heat conducting element increases the cross-sectional area of the heat conducting path or reduces the effective length of the heat conducting path. Increasing the cross-section and/or shortening the effective length of the heat conduction path results in an increased thermal flow from the heat source to the heat sink. This slows down or prevents further heating of the heat source, or reverses it into cooling of the heat source.

When the heat source cools down, the heat conducting element also cools down. Due to its physical change, the cross-section of the heat conduction path decreases and/or the length of the heat conduction path increases. This reduces the thermal flow from the heat source to the heat sink. In this way, further cooling of the heat source may be slowed down, prevented or reversed into heating.

Ideally, the materials used and the physical dimensions are selected in such a way that the heat conducting element already reacts to slight temperature fluctuations. This makes it possible that the temperature of the heat source may be kept at least approximately constant or may be kept within a given tolerance range. Since a further component may in principle be cooled with the same apparatus, the heat dissipation at a first component takes place in principle independently of a cooling of the second component, but the apparatus has the effect that both components are cooled to at least approximately the same temperature.

In some embodiments, temperature control may be achieved by making selective use of expansions due to temperature changes. This temperature control keeps the temperature in devices requiring precise positioning at a certain temperature or within a certain temperature range, thus reducing or preventing changes in length due to temperature changes (e.g., due to thermal expansion, etc.) that could alter the positioning or adjustment of these devices.

In some embodiments, the heat conducting element lies planar against the heat source and/or heat sink. Preferably, the heat conducting element lies with one surface against one surface of the heat source. In particular, the surface of the heat conducting element is then arranged to slide over the surface of the heat source, whereby the two surfaces remain in physical contact even during temperature changes.

In an exemplary embodiment, the heat conducting element has a heat pipe for increasing the heat dissipation or is flowed through by a fluid.

With this embodiment, the thermal flow from the heat source to the heat sink may be increased.

In another exemplary embodiment, the heat source has a first recess in which a first section of the heat conducting element is arranged, or the heat conducting element has a first recess in which a first section of the heat source is arranged.

This embodiment may make it possible in a constructively simple way to arrange the heat source and the heat conducting element in physical contact with each other in such a way that this contact is always maintained even with temperature changes. The heat conducting element expands preferably along the depth of the recess, whereby a planar contact between the heat conducting element and the heat source on the sides of the recess is continuously maintained. The first recess is preferably elongated, especially in the form of a prism, a cylinder or a cuboid.

In another exemplary embodiment, the heat sink has a second recess in which a second section of the heat conducting element is arranged, or the heat conducting element has a second recess in which a second section of the heat sink is arranged.

As described above regarding the first recess in the interaction between the heat source and the heat conducting element, this embodiment also offers a good possibility to ensure the continuous physical contact between the heat conducting element and the heat sink even at changing temperatures.

In another exemplary embodiment, the second recess is led through the heat sink and the heat conducting element is led through the heat sink in the second recess.

With this embodiment, the heat conducting element may also be slid with one surface over the inner surface of the recess of the heat sink. In addition, the heat conducting element may now be attached to an abutment at its end facing away from the heat source.

In another exemplary embodiment, the heat source, the heat sink and the heat conducting element are arranged along a straight line, in particular along a common longitudinal central axis.

This embodiment may make it easy to establish a physical interaction between the heat source, the heat sink and the heat conducting element. In particular, it may be achieved that an expansion of the heat source leads to a shortening of the heat conducting element and/or a shortening of the heat source leads to an expansion of the heat conducting element.

In another exemplary embodiment, the heat source, the heat sink and the heat conducting element are arranged within a housing, wherein a side of the heat source facing away from the heat conducting element and/or a side of the heat sink facing away from the heat conducting element is arranged on the housing.

This configuration may provide an abutment for the heat source and/or the heat sink. In this way, a fixed point may be created for the heat source and/or the heat sink. Therefore, especially an effect of a change in length of the heat source on the heat conducting element may be well adjusted.

In another exemplary embodiment, an imaging sensor is configured on the side of the heat conducting element facing away from the heat source. This imaging sensor has a line of sight that is directed out of the housing through an opening in a wall of the housing.

This embodiment may allow the imaging sensor to be kept at a substantially constant temperature or within a certain temperature range. This keeps the line of sight of the imaging sensor essentially constant. Furthermore, when a second imaging sensor forms part of the heat source, or a second imaging sensor forms a second heat source of a second such apparatus, the first imaging sensor and the second imaging sensor are temperature controlled in a similar manner. This allows the first imaging sensor and the second imaging sensor to be kept at substantially the same temperature even if they have different heat outputs.

In another exemplary embodiment, the apparatus further comprises a control element which absorbs thermal energy from the heat source and applies increasing pressure to the heat conducting element as the temperature rises. As described herein, the control element may correspond to a physical structure or member that, when subjected to a particular temperature, moves from a first position to a second position. In some embodiments, the control element may correspond to a bimetallic strip, a thermally-expanding metal or combination of metals, or other thermally-activated actuator that mechanically displaces (e.g., moves, expands, bends, contracts, etc.) when subjected to predetermined temperatures or temperature ranges.

This embodiment may make it possible to shorten the length of the heat conduction path between the heat source and the heat sink. This is achieved by the pressure exerted by the control element, which compresses the heat conducting element. By shortening the heat conduction path, the thermal flow increases. In this way, heating of the heat source is slowed down, suppressed or turned into cooling. When the heat source cools down, the control element also cools down and the pressure on the heat conducting element is reduced. This causes the heat conducting element to expand in the direction of its original shape, so that the length of the heat conducting path is now increased. As a result, the cooling of the heat source is slowed down, suppressed or reversed into a warming.

In another exemplary embodiment, the apparatus has a lever with a first lever arm and a second lever arm, whereby the control element exerts increasing pressure on the first lever arm as the temperature rises, so that the second lever arm exerts a pressure on the heat conducting element via the heat sink.

This embodiment may make it possible to increase the pressure that the control element indirectly exerts on the heat conducting element. In exemplary configurations, the ratio of a second length of the second lever arm to a first length of the first lever arm is at least 1, preferably at least 1.5, particularly preferably at least 2 and in particular at least 2.5.

In another exemplary embodiment, the apparatus further comprises a control element which absorbs heat energy from the heat source, and at least a section of the control element moves towards the heat conducting element as the temperature rises or a pressure on the heat conducting element is increased.

In this embodiment, the control element may act in particular directly on the heat conducting element. This allows the embodiment to be simplified.

In another exemplary embodiment, the control element is configured as a first strip and has a counter element which is fixedly arranged as a second strip on the control element, the counter element being made of a material which has a different coefficient of thermal expansion than the control element, the control element being arranged with the counter element in such a way that the control element presses against the heat conducting element with increasing pressure as the temperature rises.

This embodiment may exploit a physical principle similar to that of a bi-metal strip. Since the counter element has a different coefficient of thermal expansion, especially in the working temperature range of the apparatus, the fixed connection between the control element and the counter element leads to a deformation of the control element, especially to a curvature. This resulting force is used to exert a pressure against the heat conducting element. The pressure compresses the heat conducting element and the heat conduction path is shortened. In exemplary embodiments, the control element and the counter element form a bi-metal strip.

In another exemplary embodiment, the heat conducting element is configured as a heat conducting pad, the thickness of which decreases as the pressure exerted by the control element increases.

This embodiment may allow for a robust design. The heat-conducting pad may be compressed as the pressure increases and expands in the direction of its original shape as the pressure decreases.

In another exemplary embodiment, the heat conducting element comprises a first comb-like element and a second comb-like element configured complementary to each other and meshing with each other, the first comb-like element being arranged on the control element and the second comb-like element being arranged on the heat sink, the first comb-like element and the second comb-like element being further interlocked as the pressure through the control element increases.

In this embodiment it may be made use of, on the one hand, that the cross-sectional area of the heat conduction path increases the further the comb-like elements are pushed into one another or the further they mesh with one another.

According to another aspect there is provided a videoendoscope with an apparatus according to one of the preceding claims, the heat source having an imaging sensor. In some exemplary embodiments, the heat source is configured as an imaging sensor. In other exemplary embodiments, the heat source is configured as a first imaging sensor and a second imaging sensor or the heat source has a first imaging sensor and a second imaging sensor. In other exemplary embodiments of the videoendoscope, the videoendoscope has a second apparatus in addition to the first apparatus mentioned, in which the heat source is configured as a second imaging sensor.

According to a third aspect, the use of a previously described apparatus for heat dissipation in a videoendoscope is disclosed.

It is understood that the features mentioned above and the features to be explained below may be used not only in the combination indicated in each case, but also in other combinations or in isolation, without leaving the scope and spirit of the present disclosure.

BRIEF DESCRIPTION OF THE DRAWINGS

Exemplary embodiments according to the disclosure are shown in the drawings and are explained in more detail in the following description. There is shown.

BRIEF DESCRIPTION OF EXEMPLARY EMBODIMENTS

Figure 1:
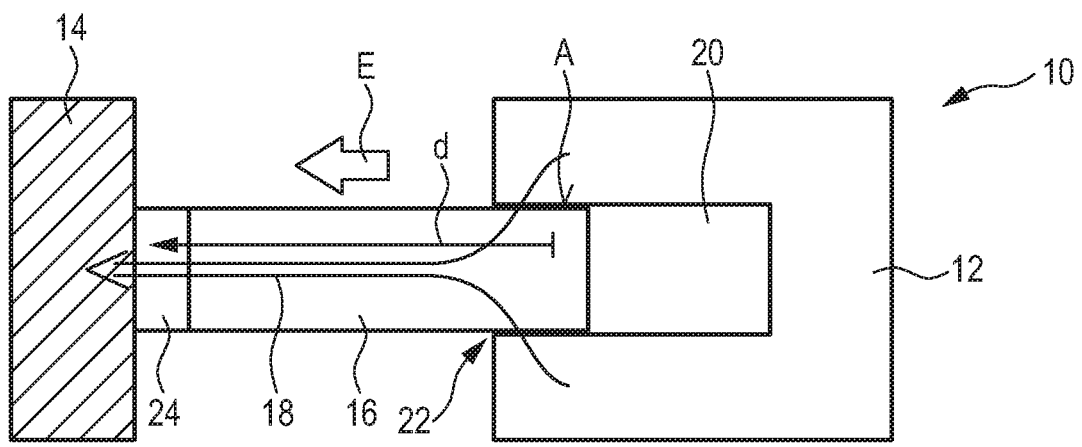
FIG. 1 shows a first embodiment of an apparatus at a lower temperature.

FIG. 1 shows a first embodiment of an apparatus 10 for heat dissipation with a heat source 12, a heat sink 14 and a heat conducting element 16. the heat conducting element leads heat energy E along a heat conducting path 18 from the heat source 12 to the heat sink 14.

The heat conducting element 16 is arranged in such a way at the heat source 12 and the heat sink 14 and changes physically with increasing temperature of the heat conducting element 16 in such a way that at least one of the two following changes results:

a) a first cross-sectional area A between the heat source and the heat conducting element 16 increases and/or a second cross-sectional area between the heat conducting element 16 and the heat sink 14 increases (not shown here)

b) a length d of the heat conduction path 18 is shortened.

The heat source 12 has a first recess 20, in which a first section 22 of the heat conducting element 16 is arranged. The heat conducting element 16 may comprise a material that, when subjected to a particular temperature or range of temperatures, expands and/or contracts at a rate defined by an associated coefficient of thermal expansion.

In this first embodiment, the main feature is that the first cross-sectional area A increases as the temperature rises. In this first embodiment, the heat conducting element 16 is connected to the heat sink 14 via an optional heat conducting pad 24.

Figure 2:
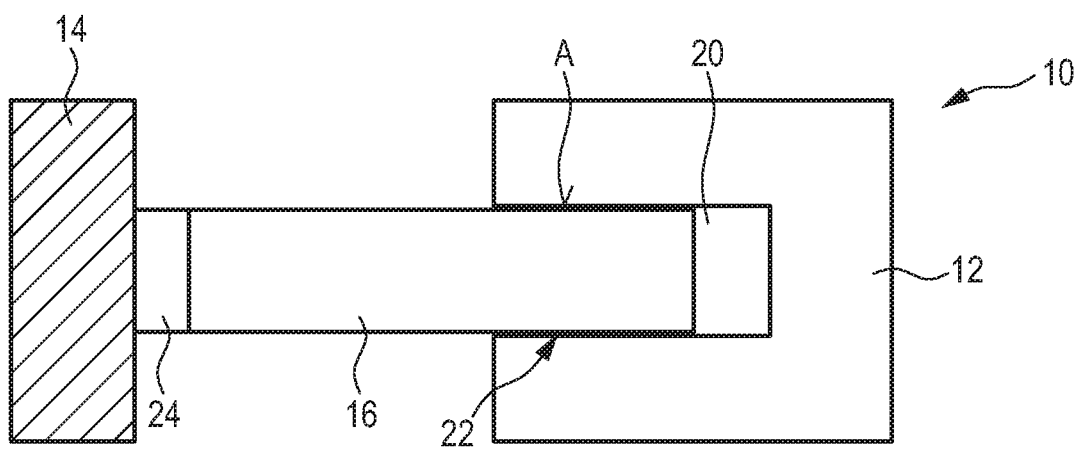
FIG. 2 shows the first embodiment at a higher temperature.

FIG. 2 shows the situation when the temperature of the heat source 12 and thus also the temperature of the heat conducting element 16 increases in the first embodiment according to FIG. 1. It may be seen that the heat conducting element 16 has extended into the recess 20 of the heat source 12. In FIG. 2, the heat conducting element 16 may expand (e.g., in the horizontal direction shown in FIGS. 1 and 2) causing the end of the heat conducting element 16 to further engage the recess 20 of the heat source 12 and increase the contact surface area between the heat conducting element 16 and the heat source 12 (e.g., between an outer peripheral surface, or surfaces, of the heat conducting element 16 and an internal surface, or surfaces, of the recess 20, etc.) There is still at least one physical planar contact between the heat conducting element 16 and the heat source 12.

Since the first cross-sectional area A between the heat source 12 and the heat conducting element 16 has now increased, there is also a larger thermal flow between the heat source 12 and the heat sink 14. In other words, the heat source 12 is now cooled more strongly, or quickly (e.g., as thermal flow increases so does the transfer of heat).

Figure 3:
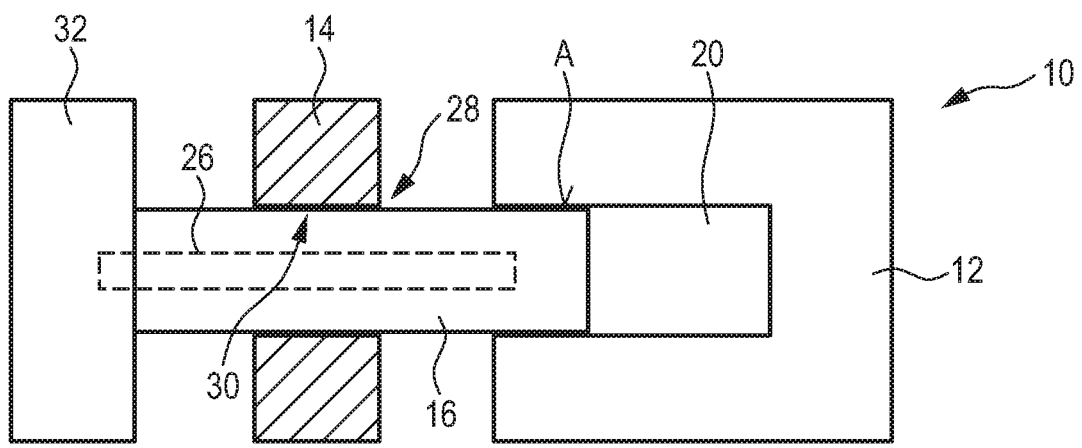
FIG. 3 shows a second embodiment of an apparatus.

FIG. 3 shows a second embodiment of an apparatus 10. Here and in the following, reference signs already introduced for the same or functionally similar elements are used and not explained again.

In the second embodiment, the heat conducting element 16 has a heat pipe 26 to increase heat dissipation. Alternatively, a fluid may also flow (not shown) through the heat conducting element 16. The heat sink 14 here has a second recess 28, in which a second section 30 of the heat conducting element 16 is arranged. Specifically, the second recess 28 is led through the heat sink 14, and the heat conducting element 16 is passed through the heat sink 14 in the second recess 28.

In contrast to the first embodiment, the heat conducting element 16 here does not have a heat conducting pad 24. Instead, the heat conducting element 16 is arranged here on a static abutment 32, which is to be understood as immovable even in case of a temperature change with respect to the heat source 12, the heat sink 14 and the heat conducting element 16.

Figure 4:
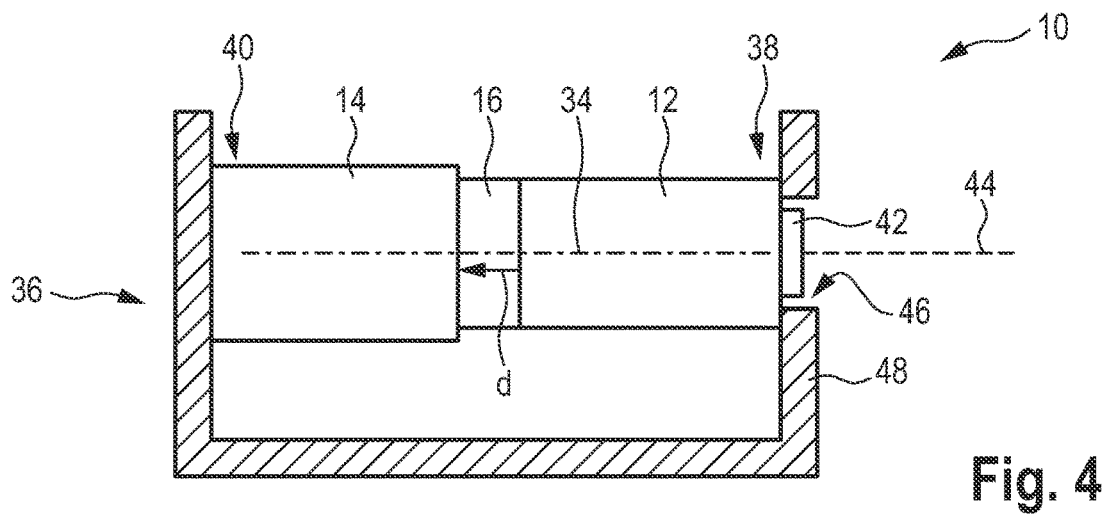
FIG. 4 shows a third embodiment of an apparatus.

FIG. 4 shows a third embodiment of the apparatus 10, whereby here the heat source 12, the heat sink 14 and the heat conducting element 16 are arranged along a straight line, in particular along a common longitudinal central axis 34. The heat source 12, the heat sink 14 and the heat conducting element 16 are here arranged within a housing 36, whereby a side 38 of the heat source 12 facing away from the heat conducting element 16 and/or a side 40 of the heat sink 14 facing away from the heat conducting element 16 is arranged on the housing 36.

Here, the heat conducting element 16 is configured as a compressible heat conducting pad. When the heat source 12 heats up and expands (e.g., in an axial direction along the line of sight 44, etc.), the heat source 12 compresses the heat conducting element 16, thus shortening the length d of the heat conducting path 18 (e.g., in the axial direction). In this way, the thermal flow from the heat source 12 to the heat sink 14 increases, so that the heat source 12 is cooled more strongly as the temperature rises. When the heat source 12 cools and shrinks, the heat conducting element 16 expands again, increasing the length d of the heat conduction path 18. In this way, the thermal flow from the heat source 12 to the heat sink 14 decreases, so that the heat source 12 is cooled less as the temperature decreases. As described herein, the shorter the length d of the heat conducting path 18, the quicker the transfer of heat. Additionally or alternatively, the longer the length d of the heat conducting path 18, the longer, or slower, the transfer of heat.

In this third embodiment, an imaging sensor 42 is arranged on the side 38 of the heat source 12 facing away from the heat element 16. The imaging sensor 42 has a line of sight 44 which is directed out of the housing 36 through an opening 46 in a wall 48 of the housing 36.

Figure 5:
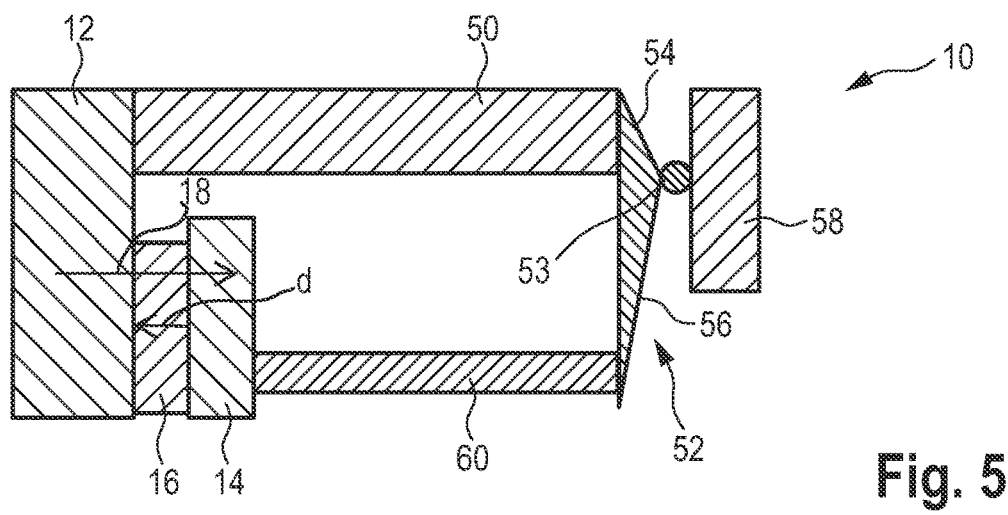
FIG. 5 shows a fourth embodiment of an apparatus at a lower temperature.
Figure 6:
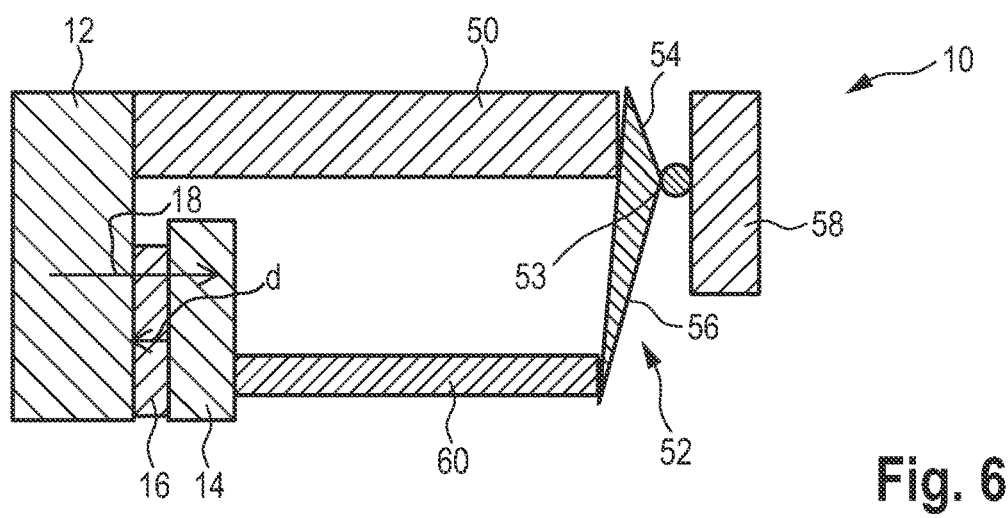
FIG. 6 shows the fourth embodiment of an apparatus at a higher temperature.

FIG. 5 shows a fourth embodiment in which the apparatus 10 also has a control element 50 which absorbs heat energy from the heat source 12 and exerts increasing pressure on the heat conducting element 16 as the temperature rises. As explained above, this causes the elastic heat conducting element 16 to be compressed as the temperature rises, thus shortening the length d of the heat conducting path 18. While the control element 50 of FIG. 5 and FIG. 6 is illustrated as a bar disposed between the heat source 12 and the lever 52, it should be appreciated that the control element 50 may correspond to any physical structure or member that, when subjected to a particular temperature, moves from a first position to a different second position. In some embodiments, the control element 50 may correspond to a thermally-expanding metal or combination of metals, or other thermally-activated actuator that mechanically displaces (e.g., moves, expands, bends, contracts, etc.) when subjected to predetermined temperatures or temperature ranges. In one embodiment, the control element 50 may mechanically displace solely through thermal expansion. Stated another way, the control element 50 may not include any moving parts, actuators, pistons, motors, or other components other than a construction, shape, and/or arrangement of the physical structure making up the control element 50.

In the fourth embodiment, a lever 52 is used for this purpose, which has a first lever arm 54 and a second lever arm 56. Here the lever 52 is arranged on a lever abutment 58. As the temperature rises, the control element 50 exerts increasing pressure on the first lever arm 54 so that the second lever arm 56 exerts pressure on the heat conducting element 16 via the heat sink 14. Stated another way, as the control element 50 increases in temperature, the control element 50 increases in size (e.g., due to thermal expansion, etc.). More specifically, as the temperature increases, the control element 50 extends in a length direction from the heat source toward the first lever arm 54 of the lever 52. This increase in length moves the first lever arm 54 toward the lower abutment 58 and as the lever 52 pivots about a fulcrum 53, or pivot point, the second lever arm 56 moves away from the lower abutment 58 (e.g., in a direction toward the heat sink 14). The pressure from the second lever arm 56 is transmitted here (e.g., to the heat sink 14, etc.) by a rigid rod 60 as an example.

FIG. 6 shows the situation with the fourth embodiment when the heat source 12 has heated up and the control element 50 has expanded as a result. It may be seen that the control element 50 has pressed against the first lever arm 54, whereby the second lever arm 56 has pressed the heat sink 14 towards the heat source 12 via the rod 60. Due to the pressure, the heat conducting element 16 is compressed, so that the length d of the heat conducting path 18 is shortened between an uncompressed state (e.g., as shown in FIG. 5) and the compressed state (e.g., as shown in FIG. 6).

Figure 7:
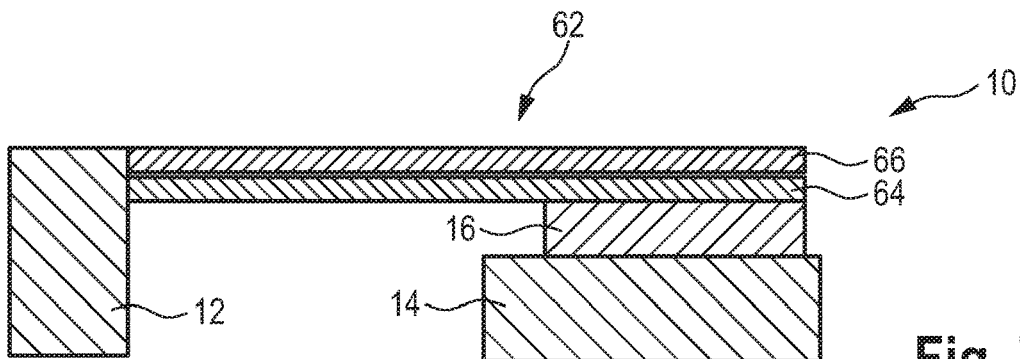
FIG. 7 shows a fifth embodiment of an apparatus at a lower temperature.

FIG. 7 shows a fifth embodiment in which the apparatus 10 also has a control element 62 which absorbs heat energy from the heat source 12 and at least a section of the control element 62 moves towards the heat conducting element 16 as the temperature rises or increases pressure on the heat conducting element 16.

Figure 8:
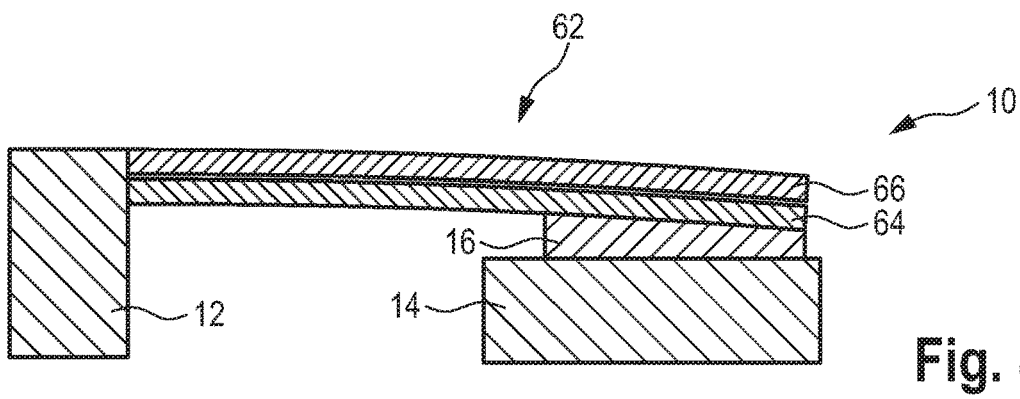
FIG. 8 shows the fifth embodiment of a device at a higher temperature.

In this fifth embodiment, the control element 62 is configured as a first strip 64 and also has a counter element 66 which is fixedly arranged as a second strip on the control element 62. The control element 62, as described herein, may correspond to a bimetallic strip that converts temperature changes into mechanical displacement. The first strip 64 and the counter element 66 of the control element 62 may be made from different materials. The counter element 66 is made of a material that has a higher coefficient of thermal expansion than the first strip 64 of the control element 62. For instance, when the first strip 64 is made from first material (e.g., steel, carbon fiber, etc.) having a first coefficient of thermal expansion, the counter element 66 may be made from a second material (e.g., copper, aluminum, etc.) material having a greater, or higher, second coefficient of thermal expansion. The control element 62 is arranged with the counter element 66 in such a way that the control element 62 presses against the thermal element 16 with increasing pressure as the temperature rises. For instance, as the temperature of the heat source 12 increases, heat transfers (e.g., through a conduction path, etc.) from the heat source 12 to the first strip 64 and the counter element 66 of the control element 62. Because the counter element 66 has a higher coefficient of thermal expansion than the first strip 64, the counter element 66 increases in length at a greater rate than the first strip 64. This difference causes a portion of the control element 62 (e.g., the end opposite the connection to the heat source 12, etc.) to mechanically displace, or bend, in a direction toward the heat sink 14 (e.g., compressing the heat conducting element 16, as shown in FIG. 8). In some embodiments, this mechanical displacement may be referred to herein as a cantilevered beam deflection.

An inverse arrangement is also possible, in which the positions of control element 62, i.e. the first strip 64, and the counter element 66 are reversed. The counter element 66 is then made of a material that has a lower coefficient of thermal expansion than control element 62, for example carbon.

FIG. 8 shows the situation with the fifth embodiment when the temperature of the heat source 12 has increased and the control element 62 has compressed the heat conducting element 16. In this embodiment, heat conducting element 16 is preferably configured as an elastic heat conducting pad, the thickness of which decreases as the pressure from control element 62 increases.

Figure 9:
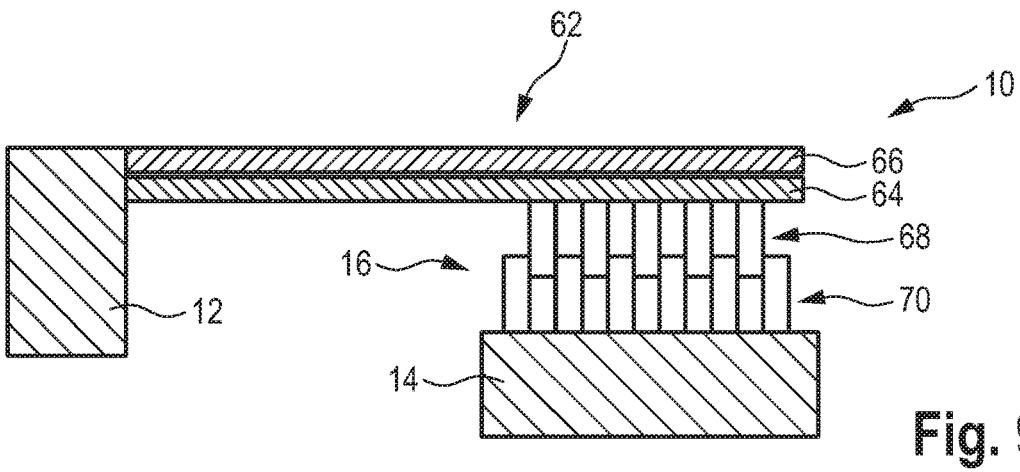
FIG. 9 shows a sixth embodiment of an apparatus at a lower temperature.

FIG. 9 shows a sixth embodiment, in which a control element 62 with a counter element 66, as described in FIG. 7, is used.

Figure 10:
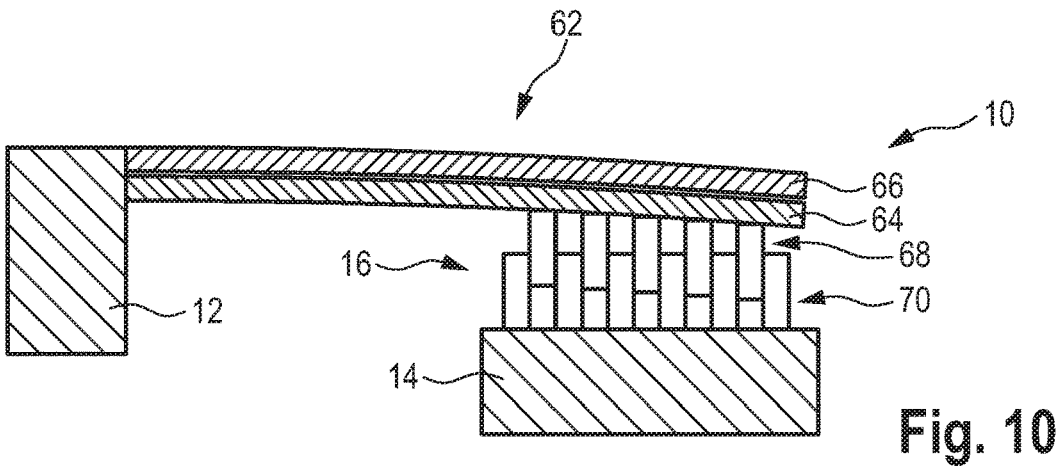
FIG. 10 shows the sixth embodiment at a higher temperature.

In the sixth embodiment, the heat conducting element 16 has a first comb-like element 68 and a second comb-like element 70, which are configured complementary to each other and comb together. Stated another way, the teeth of the first comb-like element 68 may intermesh with the teeth of the second comb-like element 70. In some embodiments, the first comb-like element 68 and the second comb-like element 70 may be referred to as combs having alternating teeth and hollows. The teeth and hollows may offset between the first comb-like element 68 and the second comb-like element 70 such that the teeth of the first comb-like element 68 align and engage with the hollows of the second comb-like element 70 and/or vice versa. Like the control element 62 of FIGS. 6-10, the teeth of the heat conducting element 16 (e.g., of the first comb-like element 68 and the second comb-like element 70) may be made from a thermally conductive material. The first comb-like element 68 is arranged at the control element 62 and the second comb-like element 70 is arranged at the heat sink 14. As shown in FIG. 10, the first comb-like element 68 and the second comb-like element 70 push further into each other as the pressure through the control element 62 increases, i.e. as the temperature of the heat source 12 rises. As the temperature of the heat source 12 rises and the counter element 66 is caused to expand, or increase in length (e.g., running in a horizontal direction shown in the figures, etc.), the control element 62 mechanically displaces, or bends, in a direction toward the heat sink 14 (e.g., providing a greater surface contact, or contact area, between the teeth of the first comb-like element 68 and the teeth of the second comb-like element 70, etc.).

Figure 11:
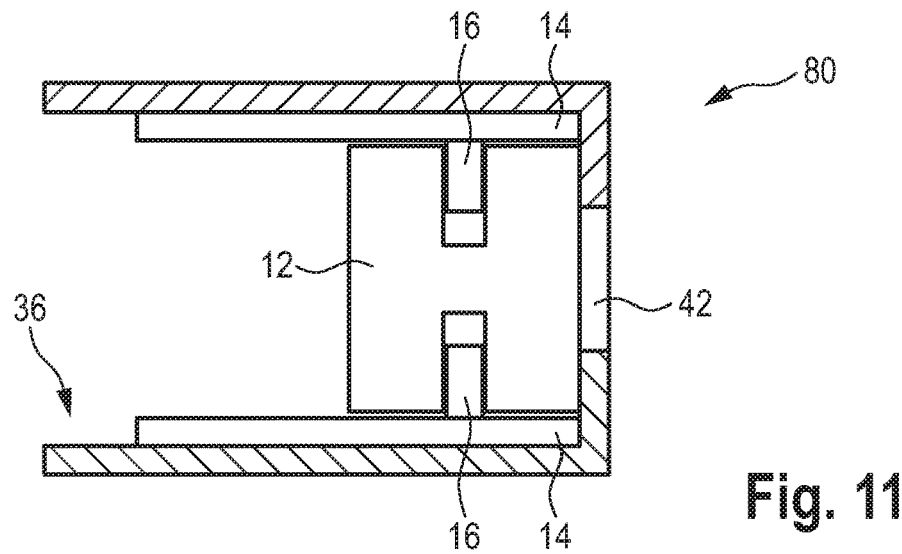
FIG. 11 shows a first embodiment of a videoendoscope.
Figure 12:
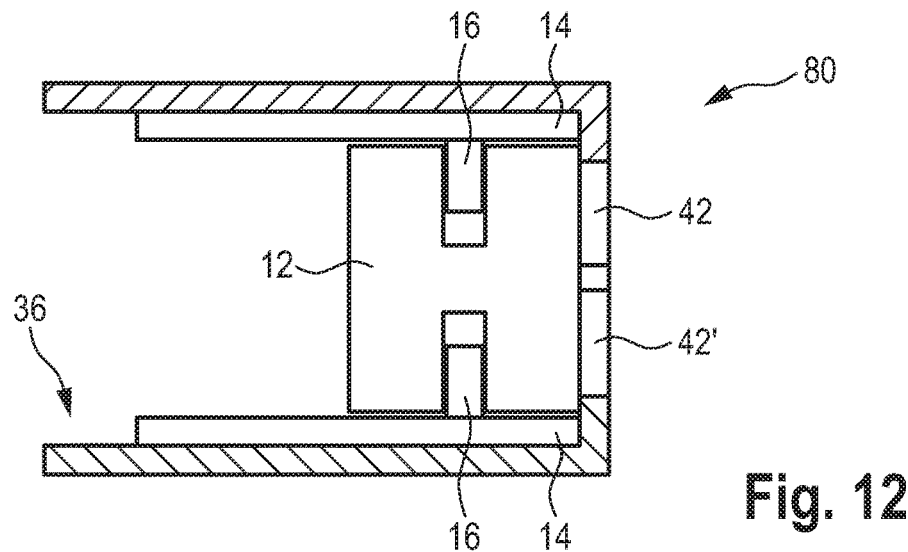
FIG. 12 shows a second embodiment of videoendoscope.
Figure 13:
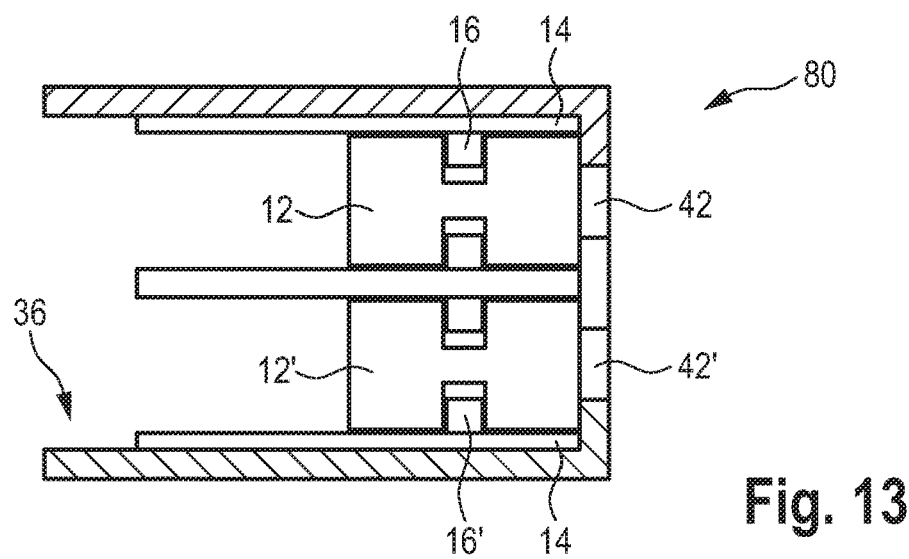
FIG. 13 shows a third embodiment of a videoendoscope.

FIGS. 11-13 show various embodiments of a videoendoscope 80 capable of employing any one or more of the heat conducting elements 16 and/or arrangements between the heat sources 12 and the heat sinks 14 as described in FIGS. 1-10. FIG. 11 shows a first embodiment of a videoendoscope 80. In a housing 36 a heat source 12 is arranged here, which has an imaging sensor 42, a heat sink 14 and a heat conducting element 16.

FIG. 12 shows a second embodiment of a videoendoscope 80, where the heat source 12 has a first imaging sensor 42 and a second imaging sensor 42'.

FIG. 13 shows a third embodiment of a videoendoscope 80, which has a first heat source 12 with an imaging sensor 42 and a second heat source 12' with a second imaging sensor 42'. In addition to the first heat conducting element 16, a second heat conducting element 16' is also shown here.

What is claimed is:

1. An apparatus adapted to dissipate heat comprising:
    a heat source,
    a heat sink,
    a heat conducting element,
    wherein the heat conducting element conducts heat energy from the heat source to the heat sink along a heat conducting path, and wherein the heat conducting element is arranged in such a way on the heat source and the heat sink and is configured to physically change in such a way with increasing temperature of the heat conducting element that at least one of: a) a first cross-sectional area between the heat source and the heat conducting element increases, b) a second cross-sectional area between the heat conducting element of the heat sink increases, and c) a length of the heat conducting path shortens,
    a control element that receives thermal energy from the heat source and exerts increasing pressure on the heat conducting element as the temperature rises, and
    a lever with a first lever arm and a second lever arm, the control element adapted to exert an increasing pressure on the first lever arm as the temperature rises, so that the second lever arm exerts a pressure on the heat conducting element via the heat sink.

2. An apparatus adapted to dissipate heat comprising:
    a heat source,
    a heat sink,
    a heat conducting element,
    wherein the heat conducting element conducts heat energy from the heat source to the heat sink along a heat conducting path, and wherein the heat conducting element is arranged in such a way on the heat source and the heat sink and is configured to physically change in such a way with increasing temperature of the heat conducting element that at least one of: a) a first cross-sectional area between the heat source and the heat conducting element increases, b) a second cross-sectional area between the heat conducting element of the heat sink increases, and c) a length of the heat conducting path shortens, and a control element that receives thermal energy from the heat source and exerts increasing pressure on the heat conducting element as the temperature rises and is configured as a first strip and has a counter element which is fixedly arranged as a second strip on the control element, the counter element being made of a material, which has a different coefficient of thermal expansion than the control element, wherein the control element is arranged with the counter element in such a way that the control element presses against the heat conducting element as the temperature rises with increasing pressure, wherein the heat conducting element comprises a first comb-like element and a second comb-like element configured complementary to each other and meshing with each other, wherein the first comb-like element is arranged on the control element and the second comb-like element is arranged on the heat sink, wherein the first comb-like element and the second comb-like element continue to slide into each other as the pressure through the control element increases.

\* \* \* \* \*